(12) United States Patent
Smith

(10) Patent No.: US 7,957,506 B2
(45) Date of Patent: *Jun. 7, 2011

(54) AUTOMOBILE SCANNING SYSTEM

(75) Inventor: Steven Winn Smith, Poway, CA (US)

(73) Assignee: Spectrum San Diego, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/732,234

(22) Filed: Mar. 26, 2010

(65) Prior Publication Data

US 2010/0177868 A1    Jul. 15, 2010

Related U.S. Application Data

(63) Continuation of application No. 12/135,196, filed on Jun. 8, 2008, now Pat. No. 7,742,568.

(60) Provisional application No. 60/943,040, filed on Jun. 9, 2007.

(51) Int. Cl.
  *G01N 23/10*   (2006.01)
  *G01N 23/087*  (2006.01)
  *H05G 1/64*    (2006.01)

(52) U.S. Cl. .................. 378/57; 378/98.9; 378/98.11

(58) Field of Classification Search ............ 378/51, 378/53, 54, 56, 57, 98.9, 98.11, 207
See application file for complete search history.

(56) References Cited

U.S. PATENT DOCUMENTS

| 4,454,606 | A | | 6/1984 | Relihan ......................... 378/97 |
| 4,626,688 | A | | 12/1986 | Barnes ...................... 250/361 R |
| 4,987,581 | A | | 1/1991 | Bernardi ......................... 378/19 |
| 5,253,282 | A | | 10/1993 | Pelc ............................. 378/98.2 |
| 5,481,584 | A | * | 1/1996 | Tang et al. .................... 378/98.9 |
| 5,661,774 | A | | 8/1997 | Gordon et al. ................. 378/101 |
| 5,687,210 | A | * | 11/1997 | Maitrejean et al. ............. 378/57 |

(Continued)

FOREIGN PATENT DOCUMENTS

EP    0 059 382    8/1985

(Continued)

OTHER PUBLICATIONS

International Search Report and Written Opinion for Application No. PCT/US2009/038903, 10 pp., dated Dec. 1, 2009 (mailing date).

*Primary Examiner* — Allen C. Ho
(74) *Attorney, Agent, or Firm* — King & Spalding LLP

(57) ABSTRACT

A dual energy x-ray imaging system searches a moving automobile for concealed objects. Dual energy operation is achieved by operating an x-ray source at a constant potential of 100 KV to 150 KV, and alternately switching between two beam filters. The first filter is an atomic element having a high k-edge energy, such as platinum, gold, mercury, thallium, lead, bismuth, and thorium, thereby providing a low-energy spectrum. The second filter provides a high-energy spectrum through beam hardening. The low and high energy beams passing through the automobile are received by an x-ray detector. These detected signals are processed by a digital computer to create a steel suppressed image through logarithmic subtraction. The intensity of the x-ray beam is adjusted as the reciprocal of the measured automobile speed, thereby achieving a consistent radiation level regardless of the automobile motion. Accordingly, this invention provides images of organic objects concealed within moving automobiles without the detritus effects of overlying steel and automobile movement.

16 Claims, 6 Drawing Sheets

U.S. PATENT DOCUMENTS

| | | | |
|---|---|---|---|
| 5,692,028 A | 11/1997 | Geus et al. | 378/57 |
| 5,838,758 A | 11/1998 | Krug et al. | 378/53 |
| 5,838,759 A | 11/1998 | Armistead | 378/57 |
| 5,910,973 A | 6/1999 | Grodzins | 378/57 |
| 6,031,890 A | 2/2000 | Bermbach et al. | 378/57 |
| 6,094,467 A | 7/2000 | Gayer et al. | 378/4 |
| 6,192,101 B1 * | 2/2001 | Grodzins | 378/55 |
| 6,249,567 B1 | 6/2001 | Rothschild et al. | 378/88 |
| 6,269,142 B1 | 7/2001 | Smith | 378/57 |
| 6,292,533 B1 | 9/2001 | Swift et al. | 378/57 |
| 6,459,764 B1 | 10/2002 | Chalmers et al. | 378/88 |
| 6,507,025 B1 | 1/2003 | Verbinski et al. | 250/358.1 |
| 6,542,580 B1 | 4/2003 | Carver et al. | 378/57 |
| 6,757,008 B1 | 6/2004 | Smith | 348/143 |
| 6,843,599 B2 | 1/2005 | Le et al. | 378/198 |
| 6,920,197 B2 | 7/2005 | Kang et al. | 378/57 |
| 6,922,461 B2 | 7/2005 | Kang et al. | 378/57 |
| 6,928,141 B2 | 8/2005 | Carver et al. | 378/57 |
| 7,010,094 B2 | 3/2006 | Grodzins et al. | 378/157 |
| 7,084,901 B2 | 8/2006 | Smith | 348/143 |
| 7,103,137 B2 | 9/2006 | Seppi et al. | 378/9 |
| 7,133,491 B2 | 11/2006 | Bernardi et al. | 378/57 |
| 7,257,188 B2 * | 8/2007 | Bjorkholm | 378/53 |
| 7,302,035 B2 | 11/2007 | Hu et al. | 378/57 |
| 7,322,745 B2 | 1/2008 | Agrawal et al. | 378/198 |
| 7,336,767 B1 | 2/2008 | Le | 378/147 |
| 7,352,843 B2 | 4/2008 | Hu et al. | 378/57 |
| 7,352,844 B1 | 4/2008 | Muenchau et al. | 378/57 |
| 7,366,282 B2 * | 4/2008 | Peschmann | 378/57 |
| 7,379,530 B2 | 5/2008 | Hoff et al. | 378/57 |
| 7,386,092 B2 | 6/2008 | Kang et al. | 378/57 |
| 7,397,891 B2 | 7/2008 | Johnson et al. | 378/57 |
| 7,408,160 B2 | 8/2008 | Verbinski et al. | 250/358.1 |
| 7,453,987 B1 | 11/2008 | Richardson | 378/98.9 |
| 7,463,715 B2 | 12/2008 | Spahn | 378/98.12 |
| 7,483,510 B2 | 1/2009 | Carver et al. | 378/57 |
| 7,483,518 B2 | 1/2009 | Hamill | 378/144 |
| 7,486,768 B2 | 2/2009 | Allman et al. | 378/57 |
| 7,486,769 B2 | 2/2009 | Brondo, Jr. | 378/57 |
| 7,526,064 B2 | 4/2009 | Akery | 378/57 |
| 7,551,715 B2 | 6/2009 | Rothschild et al. | 378/57 |
| 7,555,099 B2 | 6/2009 | Rothschild et al. | 378/90 |
| 2005/0084073 A1 | 4/2005 | Seppi et al. | 378/156 |
| 2006/0140341 A1 | 6/2006 | Carver et al. | 378/57 |
| 2007/0064868 A1 | 3/2007 | Kostka et al. | 378/53 |
| 2007/0140423 A1 | 6/2007 | Foland | 378/57 |
| 2008/0292050 A1 | 11/2008 | Goodenough et al. | 378/57 |
| 2009/0147913 A1 | 6/2009 | Dragon et al. | 378/57 |

FOREIGN PATENT DOCUMENTS

| | | |
|---|---|---|
| EP | 0 491 977 | 6/1994 |
| GB | 2 277 013 | 10/1994 |

* cited by examiner

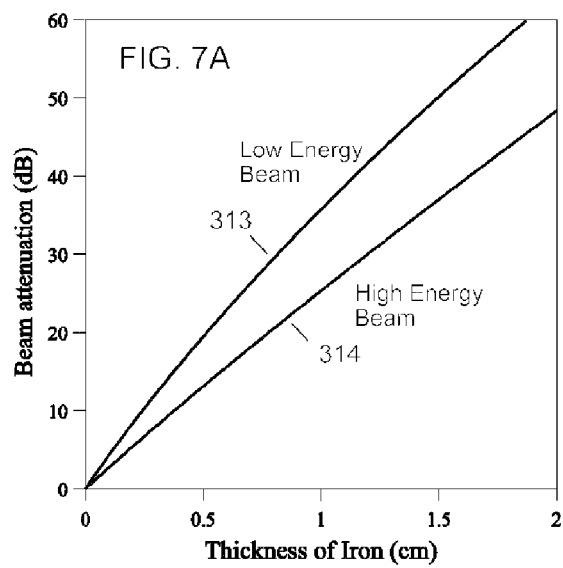
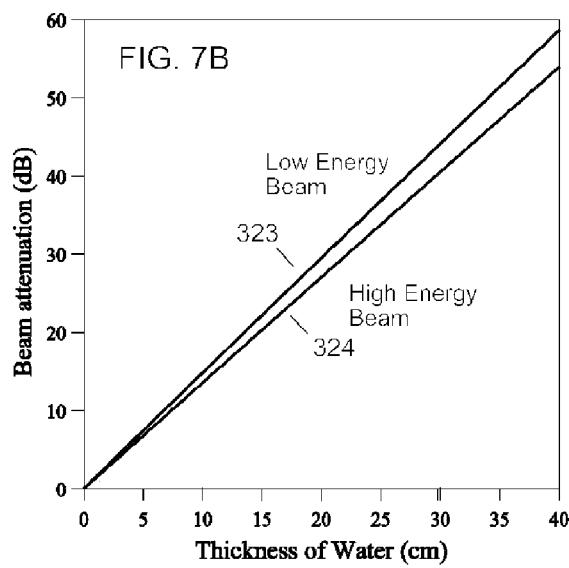
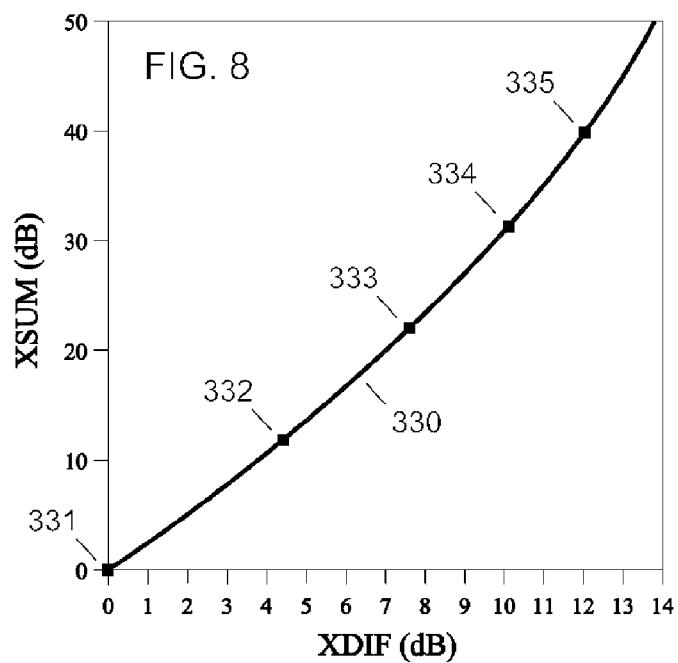

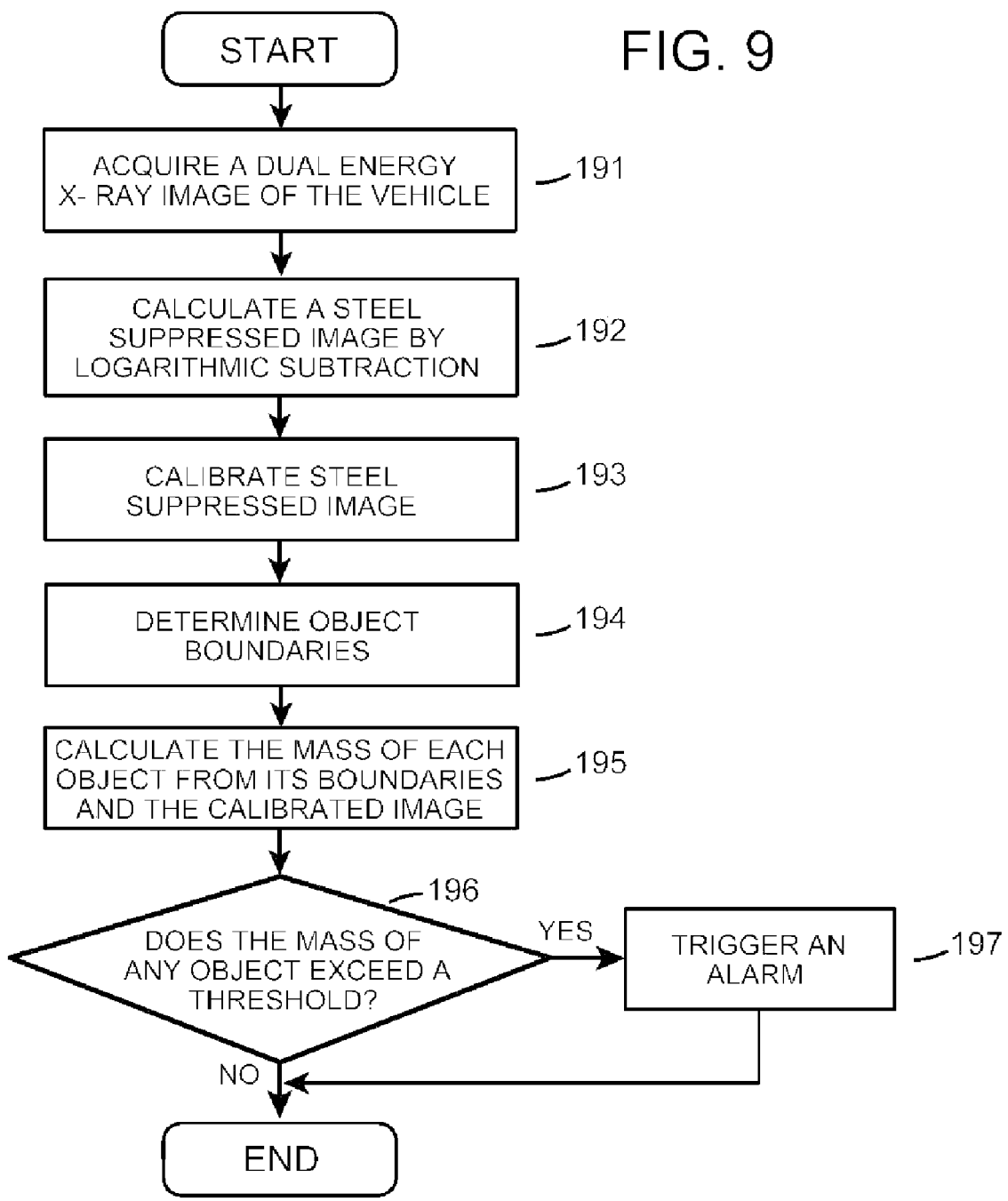

AUTOMOBILE SCANNING SYSTEM

CROSS-REFERENCE TO RELATED APPLICATION

This application is a continuation of U.S. application Ser. No. 12/135,196, filed on Jun. 8, 2008 now U.S. Pat. No. 7,742,568, which claims the benefit of U.S. Provisional Application No. 60/943,040, filed on Jun. 9, 2007, both of which are incorporated herein by reference.

BACKGROUND OF THE INVENTION

This invention relates to the x-ray imaging of automobiles to detect explosives, hidden persons, contraband, and other security threats.

Criminals and terrorists frequently conceal security threats in automobiles, such as explosives being transported into underground parking facilities for the purpose of destroying skyscrapers; illicit drugs being smuggled across borders; and illegal immigrants being brought into the country. Searching the automobile by visual inspection is time consuming and often ineffective. For instance, persons and contraband hidden in the dashboard or within the seats cannot be visually detected. X-ray inspection systems are now in use that can detect these security threats to some extent. These prior art systems use x-rays that are either transmitted through the automobile, or back scattered from the automobile, to form an image. The x-ray image is inspected by the security personnel to detect the presence of hidden security threats. However, prior art systems cannot readily distinguish the organic matter that comprises security threats from the steel forming the automobile. Further, this inability prevents the prior art systems from employing automated threat detection software programs. Still further, prior art systems are inefficient in producing contraband-revealing images at the ultra-low radiation doses that are acceptable for such security examination.

BRIEF SUMMARY OF THE INVENTION

The present Invention overcomes these limitations of the prior art by providing an apparatus and method capable of acquiring dual-energy transmission x-ray images of automobiles passing through a security checkpoint. A linescan x-ray imaging system is provided in an archway configuration, whereby the automobile being examined drives slowly through a fan beam of x-ray radiation, with the driver and passengers remaining safely within the vehicle. High-energy and low-energy x-ray spectra are alternately selected for the fan beam of radiation, allowing x-ray images of the automobile to be acquired at two separate x-ray energies. The switching spectra are formed by operating the x-ray source at approximately 120 KV, and switching the beam filtration material between 6.35 mm thick copper and 0.762 mm thick bismuth sheets, or similar elements. Detection of the fan beam of radiation is accomplished with a linear array of detectors, such as Cadmium Tungstate or Caesium Iodide crystals mounted on photodiodes. The dual-energy images are converted to a steel-suppressed image and calibrated for measuring the thickness of organic material. The mass of each organic object in the automobile is subsequently calculated from the calibrated image by summing the pixel values over the projection of the object in the image. Organic masses greater than a specified threshold trigger an alert to security personnel for secondary inspection.

The present Invention operates with only a few microRem of radiation exposure to the driver and passengers of the automobile. This radiation exposure is regarded as trivial under radiation protection standards and appropriate for general purpose security examination. One aspect of the present Invention adjusts the output intensity of the x-ray source to match the speed of the automobile, thereby maintaining the highest image quality for the allowable radiation dose.

It is therefore the goal of the invention to provide an improved method and apparatus for detecting security threats and contraband concealed within automobiles passing through a security check point. Another goal of the invention is to facilitate the inspection of automobiles for the presence of explosives, hidden persons and contraband. Yet another goal is to provide a dual-energy imaging apparatus and method capable of detecting organic objects in the presence of overlying steel. A further goal is to provide a uniform radiation exposure to automobiles being examined regardless of the automobile's speed.

BRIEF DESCRIPTION OF THE DRAWINGS

FIG. 7A and FIG. 7B are graphs in accordance with the present invention.

FIG. 8 is a graph in accordance with the present invention.

FIG. 9 is a flowchart in accordance with one aspect of the present invention.

FIG. 1 shows the overall general operation of the Invention. The scanning apparatus 100 is contained within an archway 101, about 3048 mm high and 3048 mm wide, spanning across the roadway 201. The automobile being examined 202 approaches the scanning apparatus and is stopped by a first gate-arm 204. The first gate-arm 204 is raised, allowing the automobile 202 to slowly drive through the archway 101 until stopped by the second gate-arm 205, at a position 203 after the archway 101. An x-ray assembly 103 is mounted at the top of the archway 101, directing a fan beam of x-rays downward to a linear array detector assembly 104, resting on the roadway 201. Automobile motion sensors 106 provide an electronic output of the speed of the automobile 202, 203 as it passes through the archway 101. Support members 102 hold the archway 101 upright and prevent persons on foot from entering the x-ray examination area. The x-ray image data generated by the scanning apparatus 100 is received by computer system 105 in an operator area 206. The computer system 105 processes the data to generate an image on the computer system display monitor, showing objects concealed within the automobile.

FIG. 2 shows a more detailed view of the archway 100 of the Invention. X-ray assembly 103 comprises an x-ray source 110 emitting x-rays 125 downward to a linear slit collimator 113, resulting in a fan beam of x-rays 114 passing to the linear array detector 104. A rotating chopper wheel 112 is affixed in the x-ray beam next to the x-ray source 110 and turned by a motor 111. The outlines of a large automobile being screened 202 and a person 207 are shown for size reference.

FIG. 3 shows a more detailed description of the x-ray imaging apparatus of the Invention. The x-ray source 110 is of conventional construction, such as having a fixed anode, a 1.651 mm×1.651 mm focal spot, and operating at about 120 KV and 2 ma. As known in the art, an x-ray tube operating at a selected KV results in an internal electron energy that is numerically the same. For example, it is equivalent to state that an x-ray tube operates at 120 KV, and that it operates with an electron energy of 120 keV. X-ray shielding in the design of x-ray source 110 blocks the x-ray beam 125 from all directions except downward, where it illuminates the linear slit collimator 113. Linear slit collimator 113 consists of a sheet of x-ray opaque material 121, such as lead or tantalum, with an opening 122 to permit the passage of x-rays. The opening 122 is approximately 1066.80 mm long and 2.54 mm wide, and positioned about 762 mm below the x-ray source 110. The fan x-ray beam 114 exits the linear slit collimator 113 and propagates to the linear array detector 104, located about 2286 mm below. The projected width of the fan x-ray beam 114 is therefore 2.54 mm×3048 mm/762 mm=10.16 mm where it strikes the active detection area 130 of the linear array detector 104. Focal spot blurring at this location is 1.651 mm×2286 mm/762 mm=4.953 mm. Combining the projected width with the focal spot blurring results in a total width of the fan x-ray beam 114 being 10.16 mm+4.953 mm=15.113 mm where it strikes the active detection area 130 of the linear array detector 104.

Figure 1:
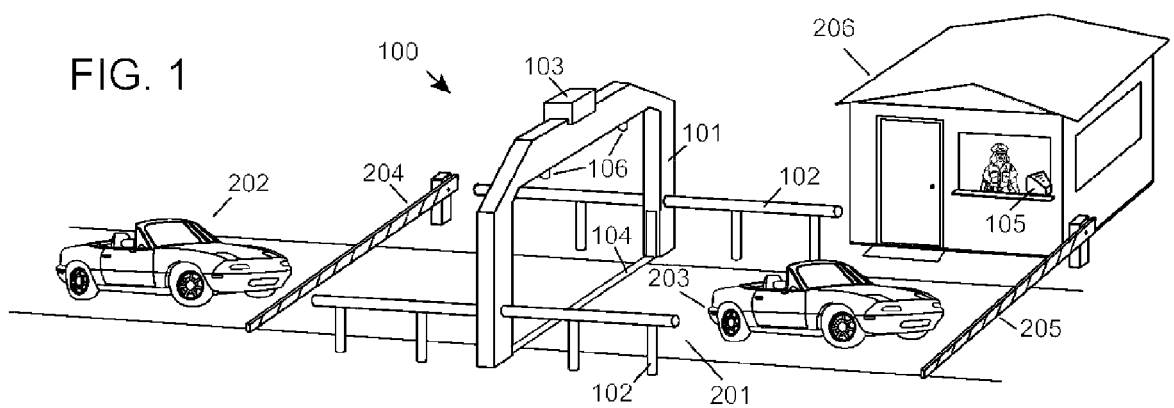
FIG. 1 is an overall schematic depiction in accordance with the present invention.
Figure 2:
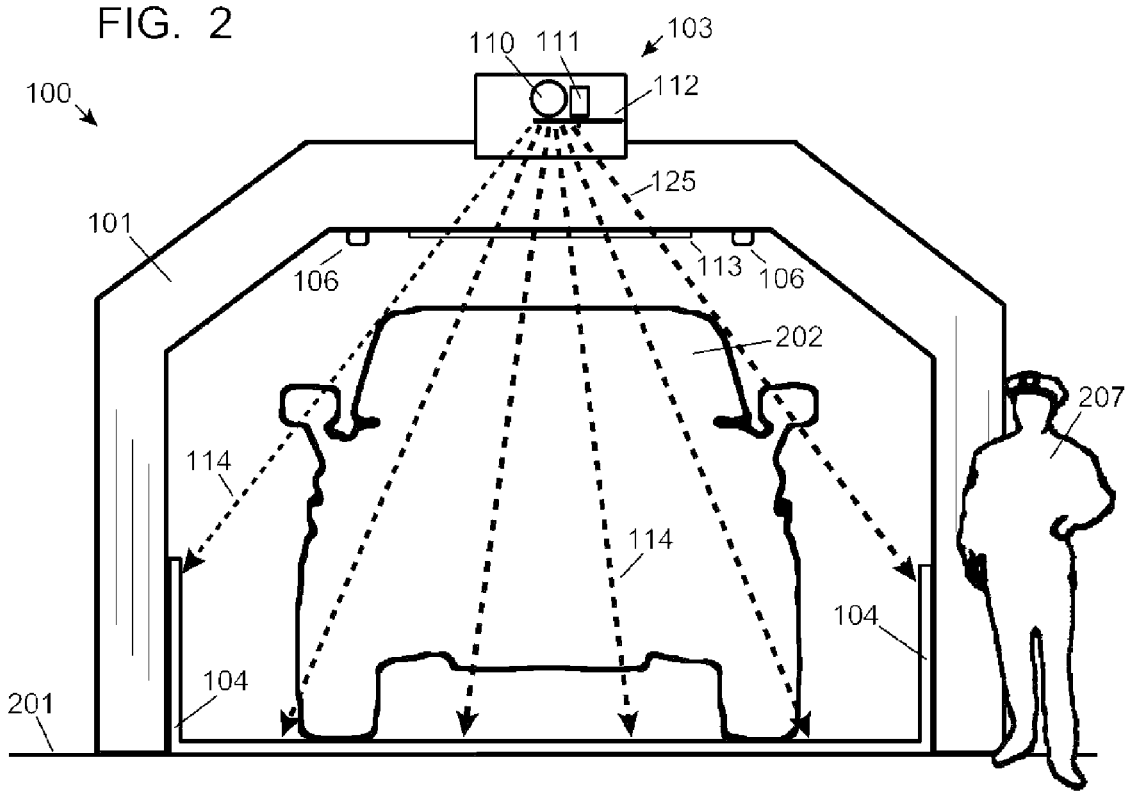
FIG. 2 is a depiction in accordance with the present invention.

The x-ray beam 125 passes through the rotating chopper wheel 112 immediately upon exiting the x-ray source 110. The rotating chopper wheel 112 consists of a copper disk approximately 355.6 mm in diameter and 6.35 mm thick. A plurality of bismuth plates 115 are affixed to the rotating chopper wheel 112 at uniformly spaced angular increments. In a preferred embodiment, four to ten such bismuth plates 115 are used, with a thickness of about 0.762 mm, with the copper under each bismuth plate removed. This results in the x-ray beam 125 passing through either 6.35 mm copper or 0.752 mm bismuth at any one instant, as the rotating chopper wheel 112 is rotated around a vertical axis 116. Rotation of the rotating chopper wheel 112 is accomplished by an electric motor 111. The rate of rotation is adjusted to provide alternating exposures of about three milliseconds through the copper beam filter followed by three milliseconds through the bismuth beam filter. In a preferred embodiment having six bismuth plates 115 this corresponds to a rotation rate of 1,250 rpm.

As thus described, the combination of the x-ray assembly 103 and the linear slit collimator 113 forms a fan beam of x-rays 114, wherein the x-ray spectrum alternates every three milliseconds between 120 KV with 6.35 mm copper filtration and 120 KV with 0.762 mm bismuth filtration. The fan beam of x-rays 114 strikes the active detection area 130 of the linear array detector 104. The active detection area 130 is about 15.24 mm wide, slightly wider than the 15.113 mm total width of the fan x-ray beam 114. In one preferred embodiment the linear array detector 104 is folded into a "U" shape. As known in the art, such folded detectors provide the same operation as flat linear array detectors, but have the advantage of being more compact. The active detection area 130 comprises a plurality of detector elements. In one preferred embodiment, 320 detector elements are used with each measuring about 15.24 mm by 15.24 mm. Each detector element can be formed by one of the known detection techniques, such as scintillators mounted on photodiodes; scintillators mounted on photomultiplier tubes; or direct detection using germanium, silicon, or cadmium zinc telluride devices. In a preferred embodiment each detector element is a 15.24 mm×15.24 mm×3.81 mm thick scintillator crystal mounted on a 9.906 mm×9.906 mm photodiode. The scintillation crystal may be either CsI(Ti) or CdWO4. A white reflective paint is applied to all exposed surfaces of the crystal to maximize light transfer from the scintillator to the photodiode. Readout electronics of such detectors are known in the art.

Figure 3:
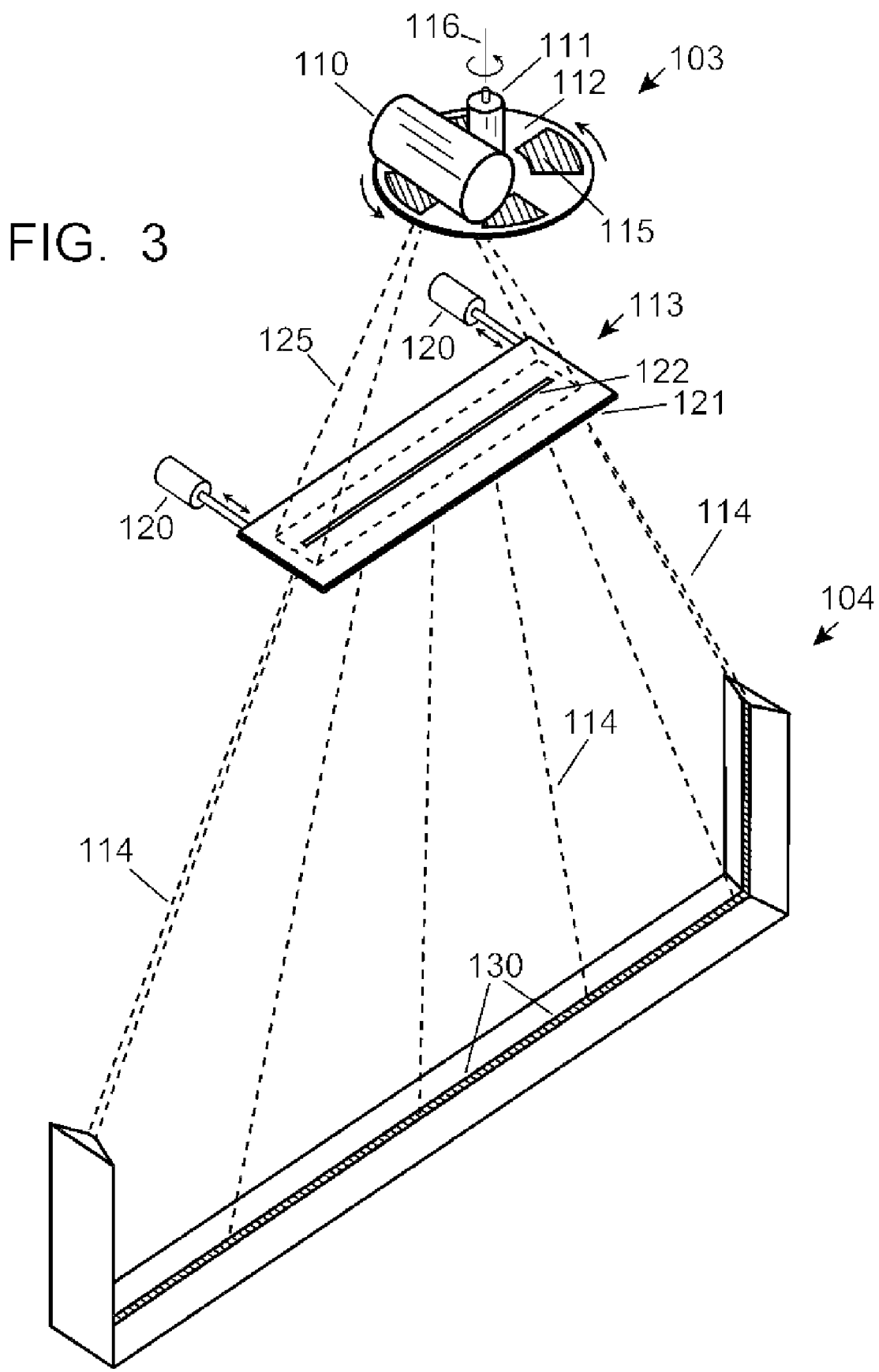
FIG. 3 is a depiction in accordance with the imaging geometry of the present invention.

The alignment of the linear slit collimator 113 is critical. Specifically, the focal spot of the x-ray source 110, the opening 122, and the active detection area 130, must remain coplanar. This alignment problem is aggravated by the automobile 202 being required to drive over the linear array detector 104, which may move the detector relative to the other assemblies. Accordingly, in one preferred embodiment a method and apparatus is provided to automatically align the linear slit collimator 113. Linear actuators 120 are affixed to the extreme ends of the linear slit collimator 113 as shown in FIG. 3. Under software control, the first linear actuator moves the first end 121 of the linear slit collimator 113 a distance of about 12.70 mm in three seconds. During this three second period the signal from the corresponding end of the linear array detector 104 is recorded and stored in relation to the instantaneous linear actuator position. Afterward, the controlling software program searches the stored data for the greatest measured signal level, and moves the first linear actuator back to the position corresponding to the greatest measured signal level. This procedure is then repeated at the opposite end of the linear slit collimator using the second linear actuator.

Figure 4:
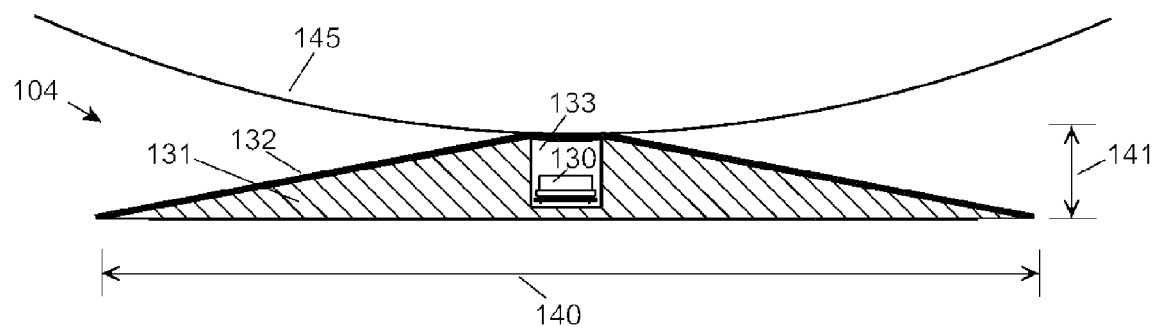
FIG. 4 is a depiction in accordance with the detector of the present invention.

FIG. 4 shows the cross-sectional construction of a preferred embodiment of the linear array detector 104. A primary goal of this design is to protect the electronic components forming the active detection area 130 from mechanical damage, while providing a smooth structure that the automobile 202 can drive over. The linear array detector 104 is formed from a solid metal base 131 having a triangular cross-section. The altitude 141 of this triangular cross-section is approximately 20.32 mm, while the width dimension of the base 140 is about 203.20 mm. A recessed channel 133 in the base measures about 198.12 mm by 16.51 mm in cross-section, providing a mounting location for the electronic components forming the active detection area 130. A 3.175 mm thick rubber sheet 132 is affixed over the metal base 131 to exclude dirt and other contamination from the active detection area 130. As the tire 145 of the automobile 202 drives over the linear array detector 104, the rigidity of the tire 145 depresses the rubber sheet 132, but does not contact the active detection area 130.

An important and key aspect of the Invention is its ability to search automobiles in a manner that is safe for the vehicle's occupants. The issue of radiation safety has been specifically addressed in the ANSI/HPS N43-17 standard entitled "Radiation Safety For Personnel Security Screening Systems Using X-rays", as well as a report prepared by the National Council on Radiation Protection and Measurements entitled "Presidential Report on Radiation Protection Advice: Screening of Humans for Security Purposes Using Ionizing Radiation Scanning Systems." These documents clearly and explicitly put forth that radiation exposures of less than ten microRem effective dose are acceptable for general purpose security screening. Accordingly, in a preferred embodiment of the Invention the radiation received by any driver or passenger is less than ten microRem effective dose, or any future value determined acceptable under ANSI/HPS N43-17. Under accepted radiation protection guidelines, infrequent effective radiation doses in the microRem range are trivial, do not need to be considered for purposes of radiation protection, and efforts are not warranted to reduce the radiation exposure.

On the other hand, using substantially less than ten microRem per examination results in a reduced ability to detect security threats in automobiles. For a constant intensity of an x-ray beam, the radiation dose is proportional to the amount of time spent in the beam. Therefore, slower moving automobiles will receive a higher dose than faster moving ones, for a fixed intensity beam. Prior art automobile scanning systems insure that the ten microRem level is met by reducing the intensity of the x-ray beam to a level that insures that the slowest moving automobiles meet the limit. In turn, this results in normal and fast moving vehicles being exposed to substantially lower radiation levels, resulting in poor detection of security threats. A preferred embodiment of the present Invention overcomes this limitation by adjusting the intensity of the x-ray beam to match the speed of the automobile.

Figure 5:
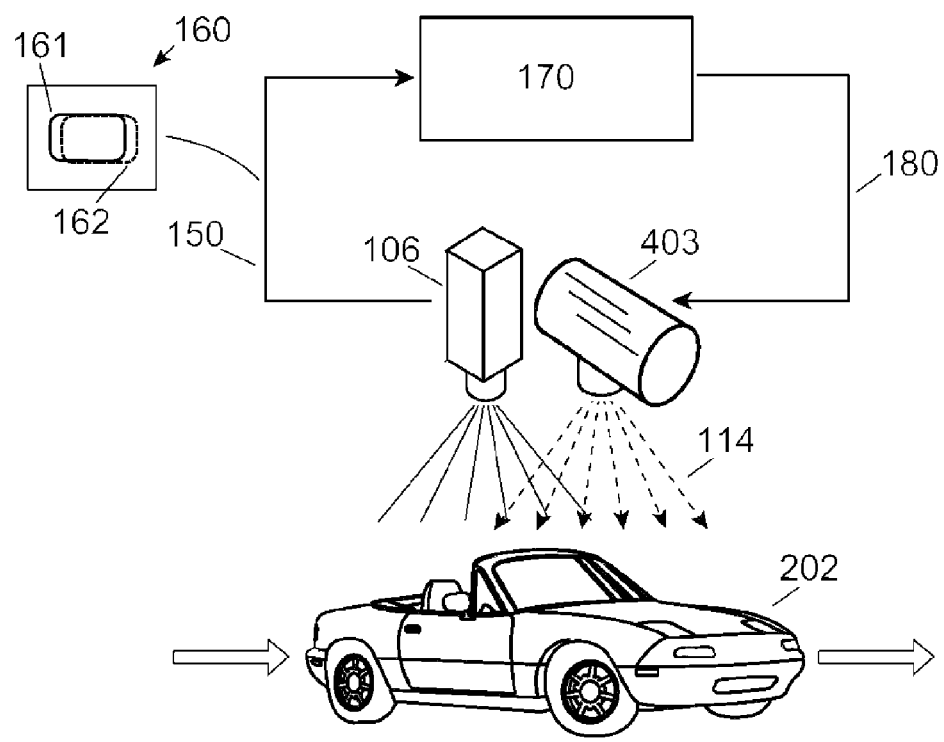
FIG. 5 is a depiction in accordance with one aspect of the present invention.

FIG. 5 explains this aspect of the Invention. The automobile being inspected 202 moves through the scanning apparatus 100 at some speed, in the range of 1 mph to 20 mph. Automobile motion sensors 106 measure this speed. In a preferred embodiment, the automobile motion sensors 106 are one or more video cameras mounted at a location where they can view the automobile 202 as it passes through the scanning apparatus 100. The video signal 150 from the camera therefore consists of a series of images 160 of the automobile 202, with a second image 162 showing the automobile displaced by a relative amount compared to a first image 161. A digital computer 170 measures this displacement in the two images 161, 162 and calculates the speed of the automobile 202 by dividing the displacement distance by the time between images. Digital computer 170 further calculates a mathematical value corresponding to the reciprocal of the speed of the automobile 202 and routes this signal 180 to a radiation intensity control 403. Radiation intensity control 403 adjusts the intensity of the x-ray beam 114 that impinges on automobile 202 according to methods known in the art, such as by changing the x-ray tube current or by moving various thickness of filtration material into and out of the beam path. The following example will explain this operation using a preferred embodiment of controlling the x-ray tube current. As an example, when the automobile 202 is moving at 20 mph, the x-ray source 110 will be controlled to operate at a current of 2 mA. However, in this same example, an automobile 202 moving at 1 mph results in the x-ray source operating at 2 mA/20=0.1 mA. The total radiation exposure received by an occupant of the automobile 202 is proportional to current divided by the speed, and will therefore be the same at all speeds between 1 and 20 mph. In this example, 2 mA/20 mph produces the same radiation dose as 0.1 mA/1 mph. In another preferred embodiment, placing approximately three cm of plastic or other organic matter in the beam path will reduce the beam intensity by a factor of two. This allows the radiation intensity control to operate over a factor of 16 in range by mechanically moving a thickness between 0 and 12 cm of plastic into and out of the beam path. This is accomplished by common mechanical techniques, such as a step wedge moved by a linear actuator, or a rotational mechanism with a cam shaped filter material.

The effective radiation dose received by occupants of the automobile is calculated as follows. From standard references known in the art, an x-ray tube operating at 120 KV and 2 mA produces a radiation exposure of 0.009 Roentgen per second at a distance of 2133.60 mm, the approximate center of the automobile. The conversion between Roentgen and Rem of effective dose is approximately unity at the x-ray energies used in the Invention. The exposure time for any location in the automobile is 0.006 seconds. This exposure time is broken into two halves, corresponding to the two energies needed to make the dual-energy measurement. During both of these halves, the intensity of the beam is reduced by a factor of about ten by filtration material inserted into the beam, as needed to shape the spectra for dual energy imaging. This results in a nominal effective dose of 0.009 Roentgens/sec× 0.006 sec×1 Rem/Roentgen×0.1=5.4 microRem effective dose. This effective dose will increase closer to the x-ray source; however, in no event will any person receive more than 10 microRem effective dose per scan.

Dual-energy x-ray imaging has long been used in security applications, for example, airport-type baggage scanners. As known in the art, an x-ray beam passing through an object is reduced in intensity according to:

$$X_1 = X_0 e\char`\^(-\mu\rho t) \quad (1)$$

where $X_0$ is the incident x-ray intensity, $X_1$ is the intensity after passing through a material of thickness, t, and density $\rho$. The parameter, $\mu$, is the mass attenuation coefficient which depends on both the atomic number of the material and the x-ray energy. Airport-type baggage scanners acquire images at two separate x-ray energies, typically about 40 keV and 80 keV. This is accomplished through the use of energy sensitive detectors having a sandwich structure, such as described in U.S. Pat. No. 4,626,688 issued to Barns. Two measurements for each pixel are therefore given by the equations:

$$XL_1 = XL_0 e\char`\^(-\mu_l \rho t) \quad (2)$$

$$XH_1 = XH_0 e\char`\^(-\mu_h \rho t) \quad (3)$$

where $XL_0$ and $XH_0$ are the intensities of the incident low and high-energy x-ray beams, respectively; $XL_1$ and $XH_1$ are the intensities of the low and high-energy x-ray beams after passing through the material, respectively; $\rho$ is the density of the material; t is the thickness of the material; and $\mu_l$ and $\mu_h$ are the mass attenuation coefficients of the material at the low and high energies, respectively. The goal of airport-type baggage scanners is to determine the atomic number of the material, or if one more than one element is present, a weighted or "effective" atomic number. This is accomplished by mathematically calculating a "logarithmic division," represented here by the variable "LD":

$$LD = \ln(XL_1/XL_0)/\ln(XH_1/XH_0) = \mu_l/\mu_h \quad (4)$$

That is, the logarithmic division measures the ratio of the high to the low-energy mass attenuation coefficients of the object being examined, which is unique for each element. For instance, carbon has a ratio of about 1.28; aluminum 2.8; and iron 6.2. This allows airport-type baggage scanners to identify different atomic elements and display them in different colors on the display monitor.

While useful for inspecting airport baggage, this technique is unworkable with the steel construction used in automobiles. First, the goals of the examination are different. Airport baggage scanners are designed to present an image display to the operator, wherein the color of each object reflects its atomic number or effective atomic number. For instance, the low atomic number elements in a water bottle or explosive appear in one color, while the steel in a handgun appears in another. However, it is pointless in automobile inspection to detect metal, since it is known beforehand that large amounts of metal are used in the construction of the vehicle. Rather, the need in automobile inspection is to detect and classify non-metal objects contained in the vehicle, in spite of the extensive overlying metal.

Figure 6A:
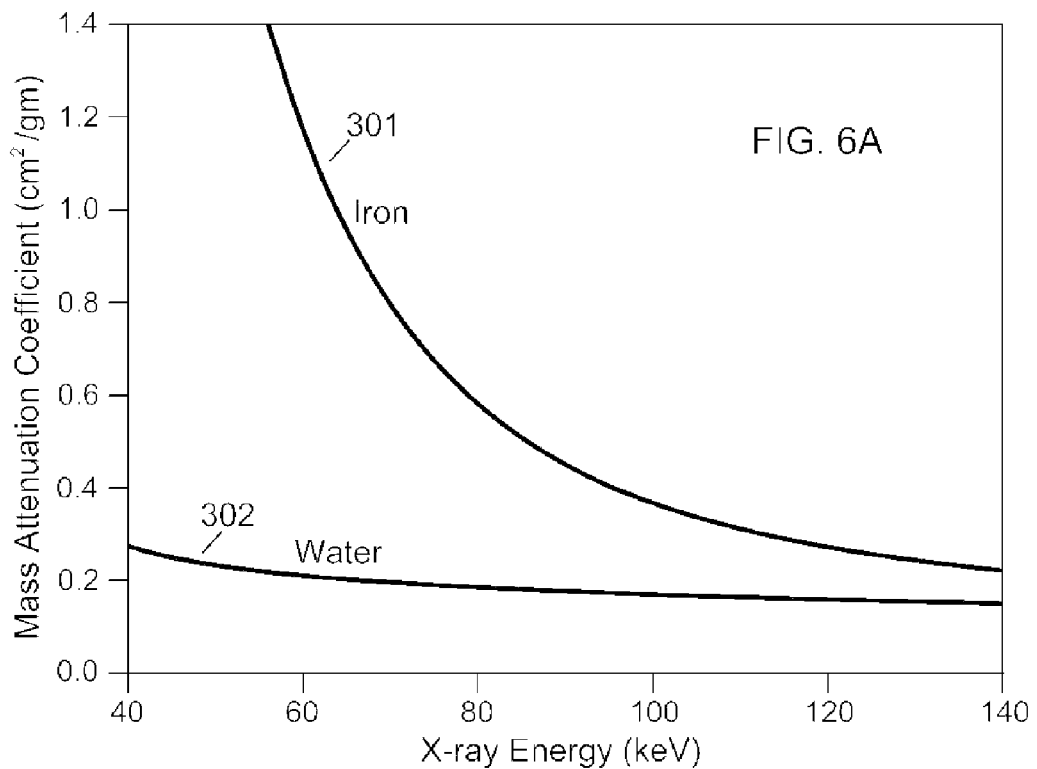
FIG. 6A and FIG. 6B are graphs in accordance with the present invention.

Second, the energy of the low-energy beam is extremely critical when imaging through the steel present in automobiles. FIG. 6A shows the mass attenuation coefficients of iron 301, which is equivalent to steel for x-ray interactions, along with water 302, which is representative of organic materials. While the curve for water 302 is relatively flat, the curve for iron drastically increases as the energy becomes lower. For instance, at 40 keV the mass attenuation coefficient of iron is 3.55 cm$^2$/gm with a density of 7.1 gm/cm$^3$. Using equation (1), a 5 mm thickness of iron will reduce the intensity of this x-ray beam to only 0.000003 of its original intensity. In typical applications about 50,000 x-rays are incident in each pixel, meaning that not even a single x-ray from the incident beam will usually penetrate through 5 mm of iron. In comparison, at 70 keV the mass attenuation coefficient is 0.795 cm$^2$/gm; the penetration is 0.06; and about 3,000 x-rays penetrate through the 5 mm of iron. Since automobile inspection requires penetration of at least 5 mm of iron, the energy of the low-energy x-ray beam must be above about 70 keV to be functional. Even though 40 keV and 70 keV may seem relatively close in numerical value, 70 keV x-rays penetrate through 5 mm of iron about 20,000 times better than 40 keV x-rays.

On the other hand, the energy of the low-energy beam cannot be higher than about 90 keV. Discriminating between two different materials, steel and water in the present case, requires that the mass attenuation coefficients of the two materials be significantly different at the energy of the low-energy beam, and relatively similar at the energy of the high-energy beam. In FIG. 6A it can be seen that the two curves 301, 302 converge as the energy becomes greater, making the energy placement of the high-energy beam relatively simple. In particular, the energy of the high-energy beam can be at any energy above about 90 keV. However, to achieve a difference in mass attenuation coefficients, the energy of the low-energy beam must be below about 90 keV. For instance, at 70 keV the ratio of the two mass attenuation coefficients is about 4.2; at 80 keV it is 3.3, and at 90 keV it is 2.8. As this ratio becomes lower, the ability of the dual-energy measurement to discriminate between the two materials becomes less.

Taking the above two limitations together, the energy of the low-energy x-beam must be placed in the narrow window of about 70 keV to 90 keV to be functional for the inspection of automobiles. If placed at a lower energy the beam will not be able to penetrate the steel of the automobile. If placed at a higher energy insufficient dual-energy information can be obtained to distinguish steel from organic materials. The techniques of the prior art, such as used in airport-type baggage scanners, do not and cannot achieve placement of the low-energy beam in this critical window.

The present Invention operates within this narrow window by using specific technique factors for generating the x-ray beam Specifically, the low-energy filter material must have a high k-edge energy, such as platinum, gold, mercury, thallium, lead, bismuth, and thorium. In addition the x-ray tube must be operated with an electron energy that is greater than the k-edge energy, but less than the k-edge energy plus about 50 keV. This approximately corresponds to operating the x-ray tube between 100 KV and 150 KV. In a preferred embodiment, the present invention uses a bismuth filter with the x-ray tube operated at 120 KV.

Third, the logarithmic subtraction used in baggage scanners provide an incorrect measurement when imaging through overlying steel. As an example, consider an explosive hidden in the trunk of an automobile. Logarithmic subtraction reports the effective atomic number of the combination of the explosive and the overlying metal. That is, the presence of the overlying steel corrupts the measurement. Further, this corruption is extreme since the attenuation of steel is far higher than the attenuation of organic material.

Figure 6B:
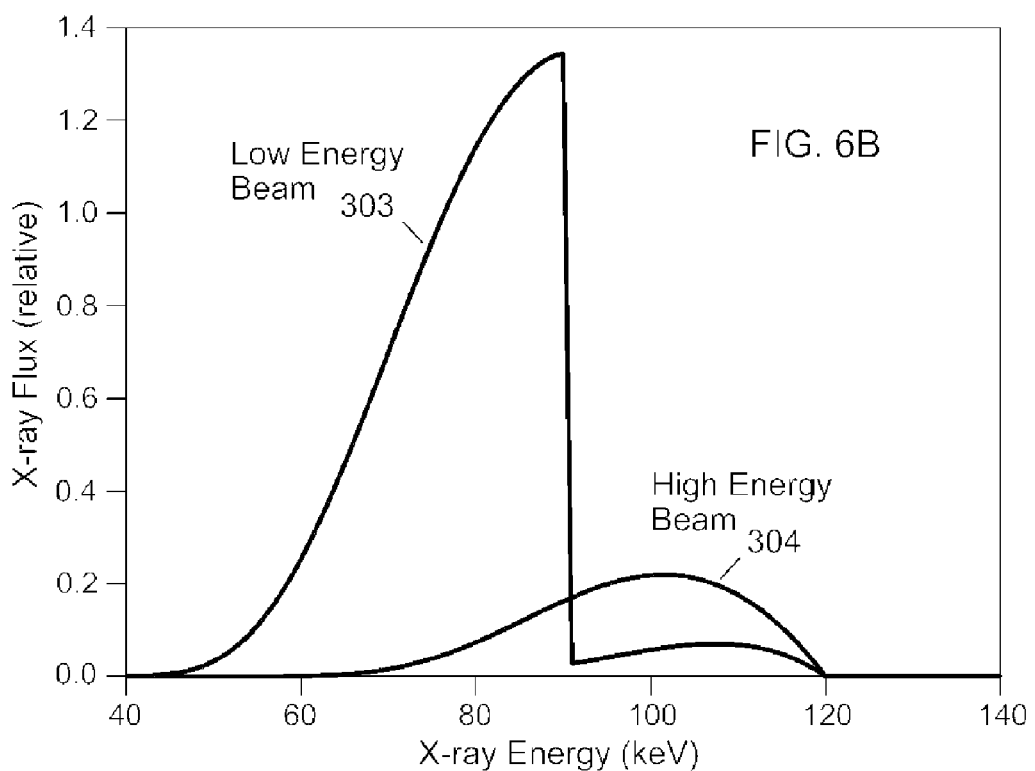

The present Invention overcomes these limitations of the prior art by providing an apparatus and method of accurately measuring the mass of organic objects concealed within the metal of an automobile. Operating the x-ray source 110 at a constant potential of approximately 120 KV, while switching filtration materials between about 6.35 mm of copper and 0.762 mm of bismuth, produces the two spectra shown in FIG. 6B. These filtration materials reduce the intensity of the incident x-ray beam by a factor of about ten, and in the process, optimally shape the spectra for the particular problem of inspecting through steel. In particular, the spectrum of the high-energy beam 304 is centered at about 100 keV. The spectrum of the low-energy beam 303 is centered at about 80 keV. A key feature of the Invention is that the bismuth filter 115 has a sharp discontinuity in its spectral filtration at 90.5 keV, a result of the bismuth k-edge at this energy. X-rays above 90.5 keV are highly attenuated, essentially removing them from the spectrum 303. As can be seen in FIG. 6B, this effect generates a low-energy beam 303 that is ideally placed in the 70 keV to 90 keV window that is critical for automobile inspection.

Another important aspect of the present Invention is the use of "logarithmic subtraction", as opposed to the "logarithmic division" previously described and used in prior art security systems. The mathematics of logarithmic subtraction are explained as follows, using the simplified example of monoenergetic x-ray beams. The following equations represent the high and low-energy beams passing through an object composed of both iron and water:

$$XH_1 = XH_0 e^{(-\mu_{hi}\rho_i t_i)} e^{(-\mu_{hw}\rho_w t_w)} \quad (5)$$

$$XL_1 = XL_0 e^{(-\mu_{li}\rho_i t_i)} e^{(-\mu_{lw}\rho_w t_w)} \quad (6)$$

where $XH_0$ and $XL_0$ are the incident intensities of the high and low-energy x-ray beams, respectively; $XH_1$ and $XL_1$ are the intensities of the x-ray beams after passing through the object; $\mu_{hi}$, $\mu_{hw}$, $\mu_{li}$, and $\mu_{lw}$ are the mass attenuation coefficients of iron and water at the high and low x-ray energies, as denoted by the subscripts; and $\rho_i$ and $\rho_w$ are the densities of iron and water, respectively. These equations can be simplified by expressing the signal for each beam as an attenuation, expressed in dB, as the beam passes through the object:

$$H = -20 \log(XH_1/XH_0) \quad (7)$$

$$L = -20 \log(XL_1/XL_0) \quad (8)$$

where H and L are the attenuation of the high and low-energy beams expressed in dB, respectively; and the other variables are as previously defined. By combining equations (5), (6), (7) and (8), and reducing by elementary algebra, the following equations are found:

$$t_w = k[H - rL] \quad (9)$$

where:

$$k = \mu_{il}/(\rho_w(\mu_{wh}\mu_{il} - \mu_{ih}\mu_{wl})) \quad (10)$$

$$r = \mu_{ih}/\mu_{il} \quad (11)$$

In (10) and (11) the parameters k and r are shown to simply be constants that depend on the fixed mass attenuation coefficients and density. Equation (9) shows the goal of the logarithmic subtraction; the thickness of the water can be calculated from the measured values and known constants, regardless of the thickness of metal present. That is, applying equation (9) to each pixel creates an electronic image where the value of each pixel is the thickness of the water, with the corrupting effect of overlying metal completely removed.

The above mathematical analysis assumes that mono-energetic x-ray beams are used, making all of the mass attenuation coefficients a fixed value. However, conventional x-ray sources produce polyenergetic x-ray beams that change their energy spectra as they pass through material, making the value of the mass attenuation coefficients a variable of the equations. This effect can be seen in FIG. 7A, showing the attenuation of the low and high-energy beams of the Inventive system 313, 314, as the beams pass through iron. Corresponding curves for water 323, 324 are shown in FIG. 7B. Two important facts can be learned from the shape of these curves. First, the attenuation in iron of both the high and low-energy beams 313, 314 are nonlinear in this graph, that is, they are not straight lines. This means that the effect of overlying steel in the Inventive system cannot be accounted for by a simple constant of proportionality, such as "r" in equations (9) and (11). A more intricate calibration method is required. However, the attenuation through water is very linear in this graph for both beams 323, 324. Accordingly, a simple constant of proportionality can adequately account for the water thickness measurement in the Inventive system. These general concepts are embodied in the following calibration procedure of a preferred embodiment of the Invention.

1. Correct for DC Offset

With the x-ray beam not energized, each detector element in the active detection area 130 will output a slightly different level of electronic signal as a result in variations in the electronic components. In a preferred embodiment, the value of the signal from each detector element is measured and stored with the x-ray beam turned off. All future measurements from the Invention are then modified by subtracting the stored values from the measured value to correct for the detector DC offset.

2. Convert to Logarithmic Domain

With no object in the fan beam 114, the value of the signal from each detector element is measured and stored with the low-energy beam turn on, referred to hereafter as $XL_0$. In a similar fashion, the value of the signal from each detector element is measured and stored with the high-energy beam turn on, referred to hereafter as $XH_0$. All future measurements from the Invention are then converted into a logarithmic attenuation. In the previous discussion for equations (7) and (8) these attenuations were expressed separately for the high and low-energy beams. However, in a preferred embodiment the calibration procedure is more easily carried out by calculating the sum and difference attenuations, as follows:

$$XSUM = -20 \log((XL_1 + XH_1)/(XL_0 + XH_0)) \quad (12)$$

$$XDIF = -20 \log((XL_1 - XH_0)/(XH_1 - XL_0)) \quad (13)$$

where $XH_1$ is a measured value of the signal from each detector element for the high-energy beam; $XL_1$ is a measured value of the signal from each detector element for the low-energy beam; XSUM is the value of the signal from each detector element for the sum of the high and low-energy beams expressed as an attenuation in dB; and XDIF is the value of the signal from each detector element for the difference between the high and low-energy beams expressed as an attenuation in dB. In other words, XSUM is the measured attenuation, expressed in dB, of the combination of both the high and the low-energy beams. Likewise, XDIF is the difference between the measured attenuations of the high and the low-energy beams, also expressed in dB.

3. Determine Calibration Data

As explained previously, the attenuation of the x-ray beams through iron cannot be expressed by a single constant. This step determines the multipoint calibration data needed to correct for this effect. In the preferred embodiment this is accomplished by acquiring images of four different thickness of iron sheets, 1/8" (3.175 mm), 1/4" (6.35 mm), 3/8" (9.525 mm) and 1/2" (12.70 mm). The value of XSUM and XDIF is measured for each thickness, taken as the average of the multitude of pixels that correspond to the object in each respective image. FIG. 8 shows the typical values of XSUM plotted against the values of XDIF for iron thickness of 1/8" (3.175 mm), 1/4" (6.35 mm), 3/8" (9.525 mm) and 1/2" (12.70 mm); 332, 333, 334, 335, respectively. Also shown is the known zero condition 331 where XSUM=0 and XDIF=0. These five points 331-335 define a curve 330 relating the value of XSUM to XDIF for all thickness of iron in the useful range of the invention. In the calibration procedure of the preferred embodiment, this curve 330 is held in a computer array with indexes 0 to 1400, corresponding to the value of XDIF being 0 to 14 dB. The value of the measured points 331-335 are inserted directly into this array, and the points between determined by a curve fit. This array defines the calibration needed to correct for various thickness of iron in the operational images, and therefore will be referred to as the "Iron Correction Factor array", represented by the notation, ICF[ ]. That is, the ICF[ ] array provides a lookup table that converts any measured value of XDIF into the corresponding value of XSUM that would occur if only iron were being measured.

As also previously explained, the attenuation of the x-ray beams through water can essentially be represented by a single constant. The calibration procedure of a preferred embodiment determines this constant by taking an image of a 101.60 mm thick container of water affixed to a 1/8" (3.175 mm) thick sheet of iron. The values of XSUM and XDIF for this calibration phantom are measured from the acquired image. The value of the calibration constant, k, is then calculated as:

$$k = 101.60 \text{ mm}/(XSUM - ICF[XDIF]) \quad (14)$$

The nominal value of k is 9.0932 mm per dB. The value of k, plus the values in the iron correction factor array, ICF[ ], form the data needed to calibrate the operation of the Invention.

4. Measure the Thickness of Organic Material in an Acquired Image

Each pixel in the image of a scanned automobile, represented by a value of XSUM and XDIF, is converted into the thickness of water corresponding to that pixel by:

$$t_w = k(XSUM - ICF[XDIF]) \quad (15)$$

This method of calibrating the dual-energy information achieves an accuracy of +/−3.81 mm, over a 0 to 304.80 mm range of water thickness, and 0 to 3/8" (9.525 mm) range of iron thickness.

A preferred embodiment of the method of inspecting a vehicle will now be described and further explained in FIG. 9. The first step is to acquire a dual-energy x-ray image of the vehicle 191. This step comprises generating x-rays of at least two different energies, directing the x-rays through the automobile, and detecting the x-ray that exit the automobile. The x-ray image acquired in this step resides as digital computer data, consisting of a plurality of pixels, with each pixel consisting of measured data for the at least two different energies.

The second step is to calculate a steel suppressed image 192. This step is carried out using the previously described logarithmic subtraction. This step may be carried out analytically, as described in equations (5)-(11). Alternatively, it may be carried out through the use of calibrated lookup tables, such as discussed in conjunction with FIG. 8 and the portion of equation (15) denoted by: "[XSUM−ICF(XDIF)]". The steel suppressed image calculated in this step resided as digital computer data, consisting of a plurality of pixels, with the value of each pixel being immune to the effect of steel in the vehicle.

The third step is to calibrate the steel suppressed image 193. In the preferred embodiment this step is carried out multiplying each pixel in the steel suppressed image by a calibration factor, referred to as "k", in equations (14) and (15). At the completion of this step, each pixel in the calibrated steel suppressed image is a direct measure of the thickness of water, organic, or other non-steel objects present in the vehicle at the location corresponding to the pixel.

The fourth step is to determine object boundaries 194. The goal of this step is to identify groups of pixels in the calibrated steel suppressed image that correspond to each of the water, organic, or other non-steel objects present in the vehicle. In the preferred embodiment this comprises thresholding the image to eliminate all regions that have a measured thickness of less than about 25.40 mm. After thresholding, groups of pixels are identified in the image that are connected. In a preferred embodiment, computer algorithms known in the art as "blob analysis" are used to further refine the object boundaries of each connected group of pixels to most closely correspond to actual objects contained in the vehicle. At the completion of this step, the pixels that correspond to each object in the vehicle are identified and reside as digital data in a computer.

The fifth step is to calculate the mass of each object from its boundaries and the calibrated image 195. The value of each pixel in the calibrated image, calculated in step 3, is the measured thickness of the corresponding object at that pixel location. The boundaries of each object determined in step 4 provide the projected area of the object. In a preferred embodiment this step 195 comprises calculating the mass of each object by summing the values of all pixels contained within the object boundaries, and multiplying by the assumed density of the object. In a preferred embodiment all organic material is assumed to have the characteristics of water, with the density of 1 $gm/cm^3$. The result of this step is a list of masses associated with each object in the vehicle, held as digital data in a computer. The assumption that all organic material has the characteristics of water results in an error that is not significant for the purposes and goals of the Invention.

The sixth step is the decision: "Does the mass of any object exceed a threshold?" 196. This step comprises a computer comparing each of the object masses calculated in step five with a predetermined mass threshold. This mass threshold depends on the application where the Invention is being deployed. For example, a border checkpoint may set the threshold to 22.680 kg to detect the presence of persons hidden in the vehicle. In comparison, the entrance to the underground parking facility of a skyscraper may set the threshold to 226.80 kg to detect car bombs.

The seventh step is to trigger an alarm 197, if the answer determined in step six is "yes." In the preferred embodiment this alarm consists of an audible sound in the area where a security officer is stationed, along with a visual presentation on a computer monitor indicating the location in the scanned image where the triggering object is located.

The above specific descriptions and embodiments have been made to explain the Invention and those skilled in the art will immediately recognize that other embodiments and modifications are within the scope of the Invention. For instance: The x-ray source may use a fixed or rotating target; operate with other combinations and variations of technique factors; be cooled by air, water, or oil; and other embodiments that are known in the art. The x-ray detector may comprise other scintillation crystals or screens; use photomultiplier tubes, other electron multiplication devices, or other light detection technologies known in the art; be mounted in other configurations to prevent damage to the components; or use other x-ray detectors known in the art. Switching the beam filtration may be done by a linear actuator, flat wheel, cylinder, or other mechanical assembly. Modulation of the intensity of the x-ray beam may be accomplished by varying the x-ray tube beam current, KV, or mechanically placing filters in the beam. Computer calculations may be carried out in alternative ways known in the art to achieve the same goals. The selection of beam filtration materials may extend to elements and compounds that have similar characteristics to those stated for the preferred embodiment of copper and bismuth. For instance, copper may be replaced by iron, nickel, zinc, silver, molybdenum, or tin, or combinations of these elements. Bismuth may be replaced by, for instance, platinum, gold, mercury, thallium, lead, bismuth, or thorium, or combinations of these elements. Calibration of the Invention may be accomplished by phantoms constructed of steel instead of iron, since iron and steel are essentially equivalent in x-ray characteristics. Further, calibration of the Invention may be made in thicknesses of organic materials other than water, such as plastics or explosives. Variations in the geometric size of the Invention may be made, such as making it large enough to examine trucks and buses. Although particular embodiments of the Invention have been described in detail for the purpose of illustration, various other modifications may be made without departing from the spirit and scope of the Invention.

What is claimed is:

1. An apparatus for imaging an organic object contained within a metal enclosure, comprising:
    an x-ray source for producing an x-ray beam passing through said metal enclosure;
    a first beam filter for creating a low-energy x-ray spectrum; said first beam filter comprising an atomic element having a high k-edge energy;
    a second beam filter for creating a high-energy x-ray spectrum;
    a filter exchanger for alternately positioning said first beam filter and said second beam filter within said x-ray beam;
    an x-ray detector for measuring an intensity of said x-ray beam exiting said metal enclosure;
    a computer for converting a digitally represented signal into a steel suppressed digital image of said metal enclosure, the computer being programmed to:
        calibrate the digitally represented signal to correct for multiple thicknesses of iron in the metal enclosure;
        calibrate the digitally represented signal to correct for organic materials in the metal enclosure;
        and further wherein the steel suppressed digital image is calculated by logarithmic subtraction;
    whereby the image of said organic object is isolated from the interference of said metal enclosure.

2. The apparatus of claim 1, wherein said metal enclosure is an automobile.

3. The apparatus of claim 1, wherein said x-ray source comprises an x-ray tube operating with an electron energy greater than the k-edge energy of said atomic element.

4. The apparatus of claim 3, wherein said x-ray tube further operates with an electron energy less than the sum of the k-edge energy and 50 keV.

5. The apparatus of claim 4, wherein said atomic element is selected from the group consisting of platinum, gold, mercury, thallium, lead, bismuth, and thorium.

6. The apparatus of claim 5, wherein an atomic composition of said second beam filter is selected from the group consisting of iron, nickel, copper, zinc, silver, molybdenum, and tin.

7. The apparatus of claim 6, wherein said filter exchanger comprises a rotating assembly.

8. The apparatus of claim 1, wherein said atomic element is selected from the group consisting of platinum, gold, mercury, thallium, lead, bismuth, and thorium.

9. The apparatus of claim 1, wherein said filter exchanger comprises a rotating assembly.

10. The apparatus of claim 1, wherein said x-ray detector comprises a linear array of scintillation crystals affixed to photodiodes.

11. An apparatus for searching an automobile for security threats, comprising:
   x-ray generating means for penetrating said automobile with x-ray radiation;
   switching filter means for changing said x-ray radiation between a low-energy spectrum and a high-energy spectrum, wherein said low-energy spectrum is substantially determined by the k-edge energy of a high atomic number element;
   x-ray detector means for converting the x-ray radiation that penetrates said automobile into a digitally represented signal;
   a computer for converting said digitally represented signal into a steel suppressed digital image of said automobile, the computer being programmed to:
      calibrate the digitally represented signal to correct for multiple thicknesses of iron in the automobile;
      calibrate the digitally represented signal to correct for organic materials in the automobile; and
      calculate the steel suppressed digital image by logarithmic subtraction.

12. The apparatus of claim 11, wherein said high atomic number element is selected from the group consisting of platinum, gold, mercury, thallium, lead, bismuth, and thorium.

13. The apparatus of claim 12, wherein said x-ray generating means comprises an x-ray tube operating between 100 KV and 150 KV.

14. The apparatus of claim 11, wherein said switching filter means comprises rotating filter means, said rotating filter means comprising a low-energy filter material and a high-energy filter material.

15. The apparatus of claim 14, wherein said low-energy filter material is selected from the group consisting of platinum, gold, mercury, thallium, lead, bismuth, and thorium.

16. The apparatus of claim 15, wherein said high-energy filter material is selected from the group consisting of iron, nickel, copper, zinc, silver, molybdenum, and tin.

* * * * *